United States Patent [19]

Wu

[11] 4,211,844
[45] Jul. 8, 1980

[54] BILIRUBIN-SPECIFIC FUNGAL ENZYME PREPARATION

[75] Inventor: Tai-Wing Wu, Rochester, N.Y.

[73] Assignee: Eastman Kodak Company, Rochester, N.Y.

[21] Appl. No.: 907,640

[22] Filed: May 19, 1978

[51] Int. Cl.² ............... G01N 31/14; C07G 7/028
[52] U.S. Cl. ............................ 435/25; 435/189; 435/191; 435/816; 435/911
[58] Field of Search ............... 195/103.5 R, 99; 435/25, 191

[56] References Cited
PUBLICATIONS

Plieninger et al., Z. Physiol. Chem. 297:238–240 (1954).
Brodersen et al., European J. Biochem 10:468–473 (1969).

*Primary Examiner*—Lionel M. Shapiro
*Attorney, Agent, or Firm*—Ronald P. Hilst

[57] ABSTRACT

A fungal enzyme preparation has specific bilirubin degrading activity and, in a preferred embodiment, generates hydrogen peroxide. Extraction methods for the enzyme preparation are disclosed. Assay compositions, elements and methods using the aforementioned enzyme preparation are also disclosed.

20 Claims, 1 Drawing Figure

BILIRUBIN-SPECIFIC FUNGAL ENZYME PREPARATION

FIELD OF THE INVENTION

This invention relates to a fungal enzyme preparation having bilirubin activity and its use in assay compositions, elements and methods.

BACKGROUND OF THE INVENTION

Bilirubin is a yellow substance which is formed in the blood by degradation of hemoglobin. The rapid and accurate detection of bilirubin in blood serum is vitally important to medical diagnosis of disease states, e.g., jaundice, in human beings.

The present invention provides new compositions and methods for the analysis of bilirubin. The invention provides enzyme preparations which unexpectedly react specifically with bilirubin and cause color changes through which one can detect and measure bilirubin.

To applicant's knowledge, there is little discussion in the literature of enzyme preparations exhibiting bilirubin activity, especially of fungal enzyme preparations which both degrade bilirubin and produce hydrogen peroxide. H. Plieninger and L. Petzold, in *Z. Physiol. Chem.*, 297:238, 1954 describe what they refer to as "mushroom enzymes" having activity on bilirubin. The enzymatic activity is reportedly obtained merely by incubating mushroom juice from the mushroom *Psalliota campestris* (now known as *Agaricus bisporus* or *Agaricus campestris*) with bilirubin. Plieninger et al mention no hydrogen peroxide generation. Plieninger et al base their findings solely on observation of oxygen uptake when a bilirubin medium was incubated with mushroom juice. They reported no oxygen uptake upon incubation of the bilirubin medium by itself. However, they failed to provide any control to measure oxygen uptake in the absence of bilirubin. Thus, it is possible that the oxygen uptake was caused by oxidation of one or more of the many possible unknown components in their crude, unpurified mushroom juice, rather than by enzymatic activity.

Furthermore, the reaction time scale reported by Plieninger et al in terms of hours is highly atypical of enzyme catalyzed reactions, which characteristically occur within minutes or less. In any case, as the comparative data in appended Example 1 show, applicant has found no evidence to substantiate the claim of Plieninger et al that simple mushroom juice exhibits enzymatic activity on bilirubin.

R. Brodersen and P. Bartels, in *Europ. J. Biochem.*, 10:468, 1969 describe an insoluble "bilirubin oxidase" isolated from guinea pig brain. They report that the insoluble enzyme converts bilirubin to a spectrum of products, including a material showing light absorption maxima at 375 nm and at 630 through 650 nm, which suggests the presence of biliverdin. They report no generation of hydrogen peroxide. (See pages 472 and 473 as well as FIG. 4 of the Brodersen et al article.)

Prior to the present invention, no bilirubin assay procedure known to applicant employed an enzymatic determination specific for bilirubin. Presumably, this is because of the small number of known enzyme preparations with specific activity for bilirubin. The most widely used assays for bilirubin are based upon the so-called diazo method or one of its many variants. This technique employs a coupling reaction of bilirubin with a diazonium salt, such as diazosulfanilic acid, to form a pigment having an extinction coefficient higher than that of bilirubin. The diazo method has a variety of problems. For example, as noted in *Clinical Chemistry-Principles and Technics*, edited by R. J. Henry, D. C. Cannon, and J. W. Winkelman, Harper and Row Publishers, 2nd Edition, pages 1042–1079 (1974), because of the many variants and the complexity of the diazo method, the determination of bilirubin for a given sample is often quite different with different variants of the method. In addition, the diazo method can be time-consuming because it typically requires several reagents which must be freshly mixed for each determination. Moreover, the diazo method can be inaccurate because serum components other than bilirubin respond to diazotization.

In view of the foregoing, an enzyme preparation which specifically degrades bilirubin and which is therefore useful in assay compositions, elements, and methods represents a valuable contribution.

SUMMARY OF THE INVENTION

The present invention provides a bilirubin-specific, enzyme preparation comprising a fungal enzyme having a protein content which, in the presence of a bilirubin-containing aqueous liquid having a pH of about 7.4 and a temperature of about 37° C., degrades at least about 0.02 micromoles of bilirubin per minute per milligram of protein.

An especially preferred embodiment of the invention provides a fungal enzyme preparation which not only degrades bilirubin but also generates detectable amounts of hydrogen peroxide.

The fungal enzyme preparation of the invention can be extracted from mushrooms. Quite unexpectedly, the novel preparation, although derived from a fungal source, is capable of acting specifically on a mammalian substrate such as bilirubin.

In accordance with a further embodiment of the invention, useful extraction methods for the fungal enzyme preparation are provided.

Another embodiment of the invention provides an assay composition for bilirubin comprising the fungal enzyme preparation. Bilirubin assay methods and elements are also included in this embodiment. In accordance with an especially preferred embodiment of this aspect of the invention, the bilirubin-specific, hydrogen peroxide-generating fungal enzyme preparation is coupled with an enzymatic hydrogen peroxide detector to provide an enzymatic assay for bilirubin.

In other embodiments of the invention the fungal enzyme preparation is used to remove bilirubin as an interferent from aqueous samples to be assayed for analytes other than bilirubin.

DETAILED DESCRIPTION OF THE INVENTION

An especially valuable property of the novel enzyme preparations is their specific activity on bilirubin. Thus, when the preparation is incubated with biliverdin or hemoglobin, both of which are highly colored and chemically similar to bilirubin, no visible change occurs. This indicates inactivity on substances closely related to bilirubin.

A fungus from which the novel enzyme preparation can be extracted is the mushroom, for example, from the well-known and abundant mushroom species, *Agaricus bisporus*.

Two different, although related, extraction methods for isolating the enzyme preparation have been developed. The preparation obtained by extraction Method II, described below, has especially high bilirubin activity and, in addition, will generate hydrogen peroxide.

Extraction of Enzyme Preparation

Specific embodiments of the two methods for extracting the novel enzyme preparation are as follows:

Extraction Method I

1. Blending Step—*Agaricus bisporus* mushroom is blended with an aqueous buffer solution having a pH of about 6.8 to about 7.8, e.g., by blending about 1 volume of mushroom with about 2 to about 3 volumes of aqueous 0.05 M sodium phosphate solution, to form a homogeneous aqueous mixture. Such blending is conveniently carried out by homogenizing the mushroom in the buffer solution, for example, using a Waring Blendor (700 Model 1120, 60 Hz Waring Products Division, New Hartford, Connecticut 06057) as a homogenization device. Of course, other equivalent blending techniques can also be employed in this step. To insure homogeneity the aqueous mixture may be filtered, for example, through cheesecloth.
2. Separation Step—Insoluble solids are separated from the homogeneous aqueous mixture of step 1, for example, by centrifuging, to obtain an aqueous liquid supernatant. The insoluble solids are discarded. Other equivalent separation techniques such as filtration can be used in place of or in combination with centrifugation.
3. Precipitation Step—Aqueous supernatant liquid of step 2 is "salted out", i.e., by adding a water-soluble salt such as ammonium sulfate to produce a precipitate. Preferably, enough water-soluble salt, sometimes referred to as a "salting out agent", is added until the liquid is from about 55% to about 60% saturated with the soluble salt. This means that, for example, about 32 to about 37 g of ammonium sulfate are added for every 100 ml of aqueous supernatant liquid from step 2. Salting out agents other than ammonium sulfate include ammonium chloride, cesium chloride and others as described in M. Dixon, E. C. Webb, *Enzymes*, 2nd Ed., Academic Press, Inc., New York, N.Y., p. 39–41 (1964).
4. Suspension Step—The precipitate of step 3 is suspended in an aqueous buffer solution having a pH of about 6.8 to about 7.8, e.g., with about 2 to about 3 volumes of aqueous 0.05 M sodium phosphate buffer solution.
5. Heating Step—The buffered suspension of step 4 is heated above room temperature (~22° C.) but below the boiling point. Preferably, the suspension is heated to a temperature in the range of from about 50° to 90° C. for about 2 up to 3 minutes.
6. Recovery Step—The aqueous suspension of step 5 is cooled and the solids are separated, for example, by centrifuging, and are discarded. Typically, such centrifuging can be effectively carried out at about 5000×g for a time of about 10 to 15 minutes. Equivalent separation techniques, e.g., filtration, may also be employed. The aqueous supernatant recovered represents a useful bilirubin-specific enzyme preparation of the invention.

Each of steps 1 through 6 of extraction Method I are conducted in air, preferably, at a temperature from about 0° to about 4° C., unless otherwise specified.

Extraction Method II

1–4. The procedures of steps 1 through 4 of Method I are followed.
5. Precipitation Step—The aqueous suspension of step 4 is admixed with a water-miscible organic liquid chilled to a temperature effective to produce a solid precipitate from the resulting aqueous-organic liquid mixture, e.g. chilled acetone having a temperature within the range of from about 10° C. to about 0° C. The aqueous-organic liquid admixture formed in this step typically contains about 30 to about 70 volume %, preferably 50 volume %, of chilled organic liquid.
6. Repeat—The solid precipitate of step 5 is resuspended and reprecipitated as in steps 4 and 5, at least once and preferably two or more times, to obtain a resultant precipitate representing a bilirubin-specific, hydrogen peroxide-generating enzyme preparation of the invention. Unlike Method I, Method II has no heating step. The temperature for each step of Method II is from about 0° to about 4° C.

Absorption and Emission Spectra

The enzyme preparation of the invention, by degrading bilirubin, yields a reaction product exhibiting characteristic absorption and emission spectra. When the enzyme preparation is incubated with a bilirubin-containing aqueous liquid at about 37° C. and about 7.4 pH in a 0.05 M sodium phosphate buffer, the reaction product exhibits an absorption peak at about 510 nm and, upon excitation with 450 nm wavelength radiation, fluoresces at about 525 nm. These characteristic absorption and emission peaks of the reaction product are observed with the enzyme preparations from either of extraction Methods I or II. Because the reaction products have not been fully characterized, however, it is not presently known whether the substance responsible for the absorption and fluorescence characteristics is a single compound or a mixture. It may well be that the particular compound in the reaction product which exhibits an absorption peak at 510 nm is different from that which fluoresces at 525 nm. Nevertheless, because neither bilirubin nor the enzyme preparation alone exhibits these absorption and fluorescent characteristics, it is evident that they belong to one or more compounds in the reaction product.

Hydrogen Peroxide Generation

Especially preferred enzyme preparations of the invention, such as those prepared by extraction Method II, not only degrade bilirubin, but also generate hydrogen peroxide. Such an enzyme preparation is particularly suited as an assay composition for bilirubin because it can readily be coupled with known hydrogen peroxide detection compositions, e.g., enzymatic hydrogen peroxide detectors. The latter contain a material having peroxidative activity, preferably peroxidase, and an indicator, e.g., a chromogenic indicator. As used herein the term chromogenic indicator includes (a) substances which change color in the presence of hydrogen peroxide and a material having peroxidative activity and (b) substances, preferably mixtures of substances, which undergo no substantial color change upon oxidation in the presence of hydrogen peroxide and a material having peroxidative activity, but which substances, upon oxidation, react with a color-forming or color-changing substance (e.g., a coupler) to give visible evidence of chemical reaction. U.S. Pat. No. 2,981,606, incorporated by reference herein, further describes representative chromogenic indicators.

Assay Compositions, Methods, and Elements

A preferred embodiment of the invention provides an assay composition and method for the detection of bilirubin in an aqueous liquid. The assay composition comprises the bilirubin-specific, fungal enzyme preparation and, if desired, one or more optional components. The assay method comprises:

(a) contacting the assay composition with a bilirubin-containing aqueous liquid sample at a pH and temperature effective for said composition to interact with bilirubin and produce a detectable change corresponding to the presence and/or concentration of bilirubin; and (b) detecting such change.

In an especially preferred embodiment, the assay composition comprises a hydrogen peroxide-generating fungal enzyme preparation of the invention and a hydrogen peroxide detection composition thereby providing a completely enzymatic assay for bilirubin.

Although the above-described assay composition and method are particularly effective at a pH of about 7.4 and a temperature from about 20° C. to about 40° C., they can be used over wider pH and temperature ranges. For example, the enzyme preparations of the invention provide useful bilirubin-degrading activity over a pH range from about 7.3 to about 8.0 and a temperature range from about 20° C. to about 50° C.

Preferably, a buffer is also present in the assay composition to maintain the pH during the assay within the effective pH range of the enzyme preparation. Phosphates such as sodium phosphate are particularly suitable. However, a variety of other buffers are appropriate and are described, for example, by Good in *Biochemistry*, 5, 467 (1966).

Hydrogen peroxide detection compositions used in certain preferred assay compositions of the invention have been described in the section "Hydrogen Peroxide Generation."

In addition to chromogenic indicators, these hydrogen peroxide detection compositions can employ other indicators. For example, a bilirubin-specific, hydrogen peroxide-generating enzyme preparation and a material having peroxidative activity can be incorporated into a membrane of an oxygen-sensitive polarographic electrode as described in Rawls, Rebecca L., "Electrodes Hold Promise In Biomedical Uses", Chemical and Engineering News, Jan. 5, 1976, page 19. The oxygen sensitive polarographic electrode serves as the indicator.

The amounts of the various components of the assay composition can vary widely. Depending upon the range of bilirubin concentrations for which the composition is intended, one uses more or less of the bilirubin-specific enzyme preparation. When using an enzyme preparation obtained by extraction Method II to analyze for a bilirubin concentration varying from about 0.1 to about 10 milligrams per deciliter, one would typically employ an assay composition containing from about 0.1 to about 0.3 mg of the enzyme preparation. This assumes that each mg of enzyme preparation has the minimum activity level for bilirubin of at least 0.02 micromoles of bilirubin per minute as determined in an aqueous liquid at a pH of about 7.4 and a temperature of about 37° C. When using a more preferred enzyme preparation of the invention having an activity level from about 2 to about 5 or more times higher than the specified minimum, proportionately smaller amounts of the enzyme preparations can be used.

Similarly, the amounts of optional hydrogen peroxide detection composition and optional buffer may vary widely. The amount of hydrogen peroxide detection composition will also depend on the bilirubin concentration for which the assay composition is intended, as well as on the purity and activity of the enzyme preparation in the assay composition.

A further embodiment of the invention provides an assay method for the removal of bilirubin as an interferent from aqueous samples to be assayed for analytes other than bilirubin. In this embodiment, the assay method comprises:

(a) treating the liquid sample with an interactive composition for the analyte of interest to produce a detectable change, e.g., a color change, corresponding to the presence and/or amount of such analyte;

(b) prior to or during treatment (a), contacting the liquid sample with an enzyme preparation of the present invention, thereby degrading bilirubin and reducing its potential for interference with the detectable change produced in (a); and (c) detecting the change produced in (a).

The interactive composition can be any composition capable of physical, electrical, chemical or other interaction with the analyte of interest leading to a detectable change, for example, a change in color, which can be related to the presence and/or amount of the analyte. Although the interactive composition can be a single compound which reacts chemically with the analyte to produce a dye or other detectable product, the term "interactive composition" is employed broadly herein to include multi-component compositions. Thus, the term includes a multi-component composition wherein a first component reacts with the analyte, and the reaction product of such reaction then reacts with a second component to produce a further reaction product which exhibits the desired detectable change. Indeed, it is not uncommon for such multi-component interactive compositions to employ three or four reaction steps leading to a final product which can be related back, to the presence and/or amount of the analyte of interest.

When an enzyme preparation of the invention is employed to eliminate or reduce bilirubin as an interferent in an assay, the interactive composition which is employed must itself be non-interfering with respect to the enzyme preparation. For example, if the analyte is to be detected by use of an interactive composition containing a hydrogen peroxide detection composition, it would clearly be inappropriate to use an enzyme preparation which itself generates hydrogen peroxide. Because the enzyme preparation of the invention can be produced to degrade bilirubin, either with or without generation of hydrogen peroxide, this particular problem can readily be avoided.

The detectable change produced in either of the two assay methods described above can be detected by a wide variety of means. A preferred embodiment of the invention employs a radiometric device capable of detecting electromagnetic energy, such as a color change, or a change in fluorescent or radioactive emission.

Because the product of interaction of the enzyme preparation of the invention with bilirubin exhibits fluorescence at about 525 nm as well as an absorption peak at 510 nm, one can use either a spectrophotometer to detect the 510 nm absorption peak or a fluorimeter to detect the emission at 525 nm. Alternatively, one can use a spectrophotometer to measure the decrease in the characteristic absorption peak of bilirubin at 445–460 nm due to the degradation of bilirubin by the enzyme preparation.

The assay composition and methods of the invention intended either for bilirubin assay or for removal of bilirubin as an interferent can be employed in liquid analytical techniques. These are sometimes called "wet chemistry". The assay composition and methods can also be employed in analytical techniques employing dry test elements, sometimes called "dry chemistry". In "wet chemistry" techniques, the assay is carried out entirely in a liquid medium; and the enzyme preparation or the assay composition containing it is employed as a liquid reagent. In such case, it is preferred to employ the enzyme preparation or assay composition in admixture with aqueous liquid at a temperature of from about 20° C. to about 40° C. and at a pH from about 7.3 to about 8.0.

When the novel enzyme preparation and assay composition are employed in "dry chemistry" techniques, they can be incorporated, for example, by imbibition, impregnation, or by coating techniques, into a reagent zone of a dry test element, e.g., a reagent layer of a dip-and-read fibrous test strip or a reagent layer of a non-fibrous multilayer element as described, in Przybylowicz et al, U.S. Pat. No. 3,992,158.

In "dry chemistry" elements, the enzyme preparation or assay composition is present as a dried residue, for example, as a lyophilized (i.e., freeze-dried) composition.

Thus, the enzyme preparation and assay composition can be prepared and used in aqueous liquid form or as a dried residue, e.g., as a freeze-dried powder. The dried residue can be packaged and stored and later reconstituted with water immediately prior to use.

The examples below further illustrate the invention. The following information is common to each example:

Protein concentration was determined by the method of Warburg and Christian (O. Warburg and W. Christian, *Biochem. Z.*, 310:384, 1941) using the ratio of absorbance at 280 and 260 nm. All chemicals were reagent grade. Bilirubin used was a product of Sigma Chemical Co., St. Louis, Missouri. All bilirubin-containing aqueous solutions were prepared with sodium phosphate buffer to have a pH of 7.4 as described by Jacobsen, J. and Wennberg, R. P., "Determination of Unbound Bilirubin in the Serum of Newborns," *Clin. Chem.*, Vol. 20, p. 783–789 (1974). All enzyme preparation extraction steps were at 0°–4°, unless otherwise specified.

EXAMPLE 1

Control Example—Measurement of $O_2$ Uptake of Bilirubin-Containing Medium in Presence and Absence of Mushroom Juice; A Repeat of Work Done by Plieninger et al, supra In this Example tests were conducted to measure the oxygen uptake of an aqueous bilirubin-containing solution in the presence and absence of mushroom juice. A control solution containing mushroom juice and no bilirubin was also monitored. 0.8 mg bilirubin (sodium salt) was dissolved in 1.5 ml phosphate buffer (pH 7.0). Mushroom juice was obtained by briefly homogenizing 3 mushrooms (*Agaricus bisporus*) in ~ 200 ml of aqueous solution containing 0.05 M Tris-HCl buffer and having a pH of 6.8. A 120 ml sample solution volume was used in each test. Using an oxygen electrode, the $O_2$ uptake was measured for the following three solutions:

Solution 1: bilirubin alone
Solution 2: mushroom juice + 1.5 cc buffer (control)
Solution 3: mushroom juice + 1.5 cc bilirubin solution The results of the electrode measurements were that bilirubin alone had no significant $O_2$ uptake for up to 12 hours; mushroom juice, with and without bilirubin, gave virtually indistinguishable $O_2$ uptake rates and amounts. That is, the presence of bilirubin produced no changes in the $O_2$ uptake that was obtained with mushroom juice alone. Thus, it was concluded that crude, unpurified mushroom juice had no enzymatic activity on bilirubin.

EXAMPLE 2

This Example describes an enzyme preparation of the invention prepared by Extraction Method I. It describes also a series of tests of the enzyme preparation and shows the effect of variables.

The following Procedures were used in Parts A-F of this Example.

Procedures

Unless otherwise indicated, all assays were performed at 37° C. and a pH of 7.4 using sodium phosphate aqueous buffer solution. The initial concentration of bilirubin in each assay reaction mixture was 2–4 mg/dl. In each assay, a reference cuvette containing an aqueous liquid control was also monitored. This control contained no bilirubin and the same level of enzyme as in the reaction cuvette. Enzyme velocity was measured by following the time-dependent decrease in absorbance either at 460 nm ($\Delta A_{460}$) or at 440 nm ($\Delta A_{440}$) due to the breakdown of bilirubin. A Beckman Acta CV spectrophotometer (Beckman Instruments Co.) was used to monitor absorbance. In each assay, the change in absorbance was monitored over at least a 5 minute incubation period. During this incubation period, there was observed little or no change in absorbance of a separate aqueous bilirubin-containing control solution free from any enzyme preparation of the invention.

Part A—Production of a Bilirubin-Specific Enzyme Preparation by Extraction Method I About 110 g of mushrooms (*Agaricus bisporus*) were washed in distilled water and blended in a Waring Blendor homogenizing device in about 1–2 volumes of 0.05 M potassium phosphate buffer at pH 6.8. The mixture was then filtered through two layers of cheesecloth and solids were separated by centrifuging at 4,050xg for 15–20 minutes at 4° C. The insoluble solids were discarded. To precipitate solids from the supernatant, sufficient $(NH_4)_2SO_4$ was added to provide 60% saturation. (Approximately 36 g of solid $(NH_4)_2SO_4$ per 100 ml of supernatant was used.) The solid precipitate was suspended in the same buffer as above, but at pH 7.4. Five ml of this suspension were heated at 65° C. for 3 minutes. Recovery was then carried out by chilling the suspension in an ice bath and centrifuging it at 16,300xg for 20 minutes at 0°–4° C. This yielded approximately 110–120 mg of an aqueous supernatant containing about 12 mg/ml protein and exhibiting the bilirubin-specific activity characteristic of the enzyme preparations of the invention.

Part B—Bilirubin Specificity Materials

Hemoglobin—obtained from freshly isolated human whole blood or purchased from Sigma Chemical Co., St. Louis, Missouri.

Biliverdin—purchased from Sigma Chemical Co.

Because bilirubin is a degradation product of hemoglobin and bilirubin is easily oxidized to biliverdin, it was important to ascertain whether the enzyme preparation prepared according to the procedure described in Part A of this Example would react with either of these compounds.

The assay procedure described in "Procedures" was used, except that hemoglobin (10–15 mg/dl) and biliverdin (1–5 mg/dl) were substituted for bilirubin. The substrates were each incubated in 0.05 M phosphate buffer, pH 7.4, 22° C. with a series of varying amounts of the enzyme preparation as described in Part A containing from 0.3 to 0.8 mg of protein. After 2–5 minutes incubation, the assay reaction mixtures were scanned against reference cuvettes containing identical compositions, except that the enzyme preparation was omitted. For hemoglobin, there was no change in absorbance at 420, 540, 580 or 620 nm (known $\lambda_{max}$ for hemoglobin). For biliverdin, no changes in absorbance at 380 or 670 nm (known $\lambda_{max}$ for biliverdin) were observed. Thus, it was concluded that the enzyme preparation as described in Part A exhibited specific activity towards bilirubin.

Part C—Effect of Enzyme Concentration

Kinetic data were obtained as described in "Procedures." Different amounts of the enzyme preparation extracted as in Part A were added to a series of constant volume assay reaction mixtures having a total volume (including bilirubin-containing buffered aqueous liquid and enzyme preparation) of 2 ml. The initial bilirubin concentration in each assay reaction mixture was 4 mg/dl.

Figure 1:
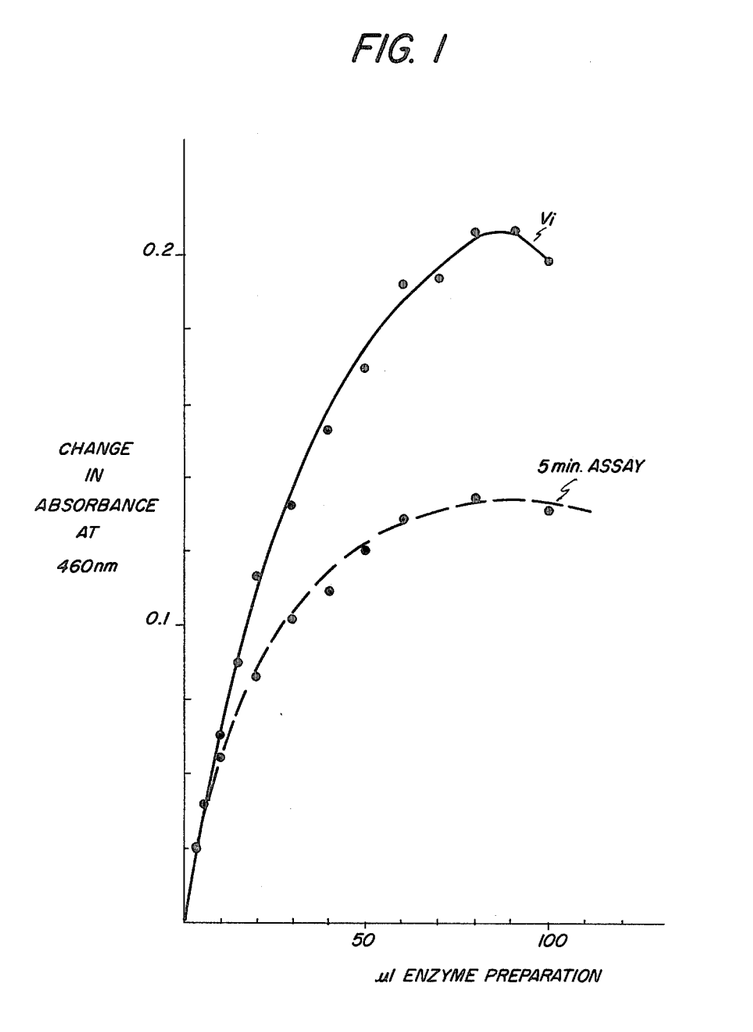
FIG. 1 is a plot illustrating the change in optical absorbance of a standard bilirubin-containing solution in response to varying amounts of a bilirubin-specific fungal enzyme preparation of the invention.

FIG. 1 shows a progressive increase in both the initial velocity, $V_i$ (i.e., change in absorbance at 460 nm per minute) and 5 minute assays (measured as total change in absorbance at 460 nm over 5 minutes) with increasing amounts of the enzyme. The response was linear up to the addition of about 15 μl of enzyme preparation (containing 0.18 mg of protein) for the initial velocity ($V_i$), and up to the addition of about 10 μl of enzyme preparation (containing about 0.12 mg of protein) for the 5 minute assay.

Part D—Effect of Bilirubin Concentration

A series of constant volume 10 μl samples of the fungal enzyme preparation of Part A (each containing approximately 0.12 mg protein) was prepared. Each 10 μl sample was then added to a 2 ml sample of aqueous liquid containing a different concentration of bilirubin. The effect of varying levels of bilirubin concentration on the enzyme preparation was then evaluated as described in "Procedures."

The relationship between $V_i$ and bilirubin concentration is shown in Table I. An increase in $V_i$ with bilirubin concentration was evident until about 4 mg/dl bilirubin concentration, which was at the upper limit of detection of the spectrophotometer. Based on a Lineweaver-Burk transformation of the available data [see Lineweaver, H. and Burk, D., *Journal of American Chemical Society*, Vol. 56, p. 658 (1934)], the apparent extrapolated Michaelis constant, $K_m$, of the enzyme for bilirubin corresponds to about 7.04 mg/dl.

Table I

| Bilirubin Concentration (mg/dl) | $V_i$ ($\Delta A_{460nm}/min$) |
|---|---|
| 0 | 0 |
| 0.5 | 0.4 |
| 1.0 | 0.7 |
| 1.5 | 0.1 |
| 2.0 | 0.12 |
| 2.5 | 0.16 |
| 3.0 | 0.17 |
| 3.5 | 0.18 |
| 4.0 | 0.19 |

Part E—Effect of pH

The bilirubin concentration for each assay reaction mixture evaluated in this Part was constant at 2 mg/dl. A series of enzyme mixtures were prepared, each containing an enzyme preparation as described in Part A and a different amount of 0.05 M phosphate buffer to provide a different pH level. All other assay conditions were as described in "Procedures." Each enzyme mixture was then evaluated in a 2 ml assay reaction mixture by adding a 10 μl sample of each enzyme mixture to a bilirubin-containing aqueous liquid as described in "Procedures." Table II shows the pH-activity profile. The optimum pH was 7.4. The sharp drop in activity at lower pH indicated either that the enzyme was more alkali-than acid-stable, and/or that the bilirubin was more soluble, and hence more available to the enzyme, at an alkaline pH.

Table II

| pH | $V_i$ ($\Delta A_{460nm}/min$) |
|---|---|
| 7.0 | 0 |
| 7.4 | 0.110 |
| 7.8 | 0.094 |
| 8.0 | 0.068 |
| 8.5 | 0.050 |
| 9.0 | 0.048 |

Part F—Effect of Temperature

All assay reaction mixtures evaluated in this Part as described in "Procedures" contained 4 mg/dl of bilirubin and approximately 20 μl of the enzyme preparation (containing about 0.24 mg of protein) described in Part A. Enzyme activity was evaluated over the temperature range of 25°–39° C. (at pH 7.4±0.05) under otherwise standard assay conditions. Table III shows that activity peaked at 37° C. However, the variation over the temperature range tested was small.

Table III

Effect of Temperature on Enzyme Reaction Rate

| Temperature (°C.) | Initial Velocity ($\Delta A_{460}$ nm/min) |
|---|---|
| 25 | 0.337 |
| 27 | 0.352 |
| 30 | 0.384 |
| 35 | 0.385 |
| 37 | 0.399 |
| 39 | 0.391 |

EXAMPLE 3

This Example describes enzyme preparations of the invention as prepared by Extraction Method II.

The following Procedures were used in Parts A-G of this Example.

Procedures

1. The peroxidase used in certain of the assays in this Example was horseradish extract obtained from Miles Laboratories, Inc., Elkhart, Indiana, having an activity of about 800 purpurogallin units/mg. Aqueous stock solutions of this peroxidase were prepared by dissolving 1 mg of the horseradish extract in 5 ml of 0.05 M sodium phosphate aqueous buffer having a pH of about 7.4. The peroxidase stock solution was diluted 50 fold immediately before use.

2. Assays for bilirubin-degrading activity were conducted in this Example as follows:

Bilirubin-containing solutions, buffered as stated above, were incubated with a sample of the enzyme preparation, and the decrease in absorbance at $\lambda_{max}$ of bilirubin (about 440 nm) was monitored with a spectrophotometer against a reference cuvette containing an aqueous control solution free from bilirubin but which was otherwise identical. The final volume of each assay reaction mixture was 1.01 ml, and unless otherwise stated, all assays were at 22°–25° C.

Part A—Production of a Bilirubin-Specific, $H_2O_2$-Generating Enzyme Preparation by Extraction Method II About 100 g of mushrooms (*Agaricus bisporus*) were washed in distilled water and blended in a Waring Blendor homogenizing device in 2–3 volumes of 0.05 M sodium phosphate buffer at pH 7.4. The mixture was then filtered through two layers of cheesecloth and solids separated by centrifuging at 6,950xg for 15–20 min. at 4° C. The insoluble solids were discarded. The supernatant was precipitated with 60% saturated $(NH_4)_2SO_4$ by adding, with constant stirring, 36 g solid $(NH_4)_2SO_4$ per 100 ml of supernatant and allowing the supernatant to stand for about 0.5 hours. The resulting precipitate was suspended in 2–3 volumes of 0.05 M sodium phosphate buffer. The thus suspended enzyme material was precipitated with ice-chilled acetone (1:1 v/v); and this precipitate was resuspended in 2 volume of 0.05 M sodium phosphate buffer and reprecipitated with chilled acetone. The final resuspension and reprecipitation steps were repeated 2 times to give an additional 2-fold purification of the enzyme preparation. The final supernatant was discarded. The remaining brownish precipitate was a bilirubin-degrading, $H_2O_2$-generating enzyme preparation of the invention and was found to contain approximately 240 to 300 mg protein. This enzyme preparation was then freeze dried until ready for use.

Part B

Two separate batches of enzyme preparation were produced as described in Part A of this Example. Table IV, below, summarizes the results of the two successive extractions. It can be seen that (1) considerable variability existed between the initial protein concentration and enzyme activity in the crude blends; (2) an 8–9 fold enhancement in enzyme activity (over the $(NH_4)_2SO_4$ salting out step) was obtained from the acetone precipitation step; and (3) total units of activity increased with progressive purification.

Table IV

Summary of Results On Two Batches of Enzyme Preparation

| Extraction Step | Total Volume (ml) | Protein mg/ml | Total mg | % Recovery of Protein | Specific Activity* (S.A.), μmoles Bilirubin Converted/min/mg Protein 25° C. pH 7.45 | Enzyme Activity** Total Units (S.A. × mg) | % Recovery of Activity | Purification Factor |
|---|---|---|---|---|---|---|---|---|
| 1. Crude Blend | | | | | | | | |
| Batch 1 | 500 | 3.69 | 1845 | 100 | 0.0015 | 2.768 | 100 | 1 |
| Batch 2 | 500 | 6.50 | 3250 | 100 | 0.005 | 16.25 | 100 | 1 |
| 2. $(NH_4)_2SO_4$ Fractionation (0–60%) | | | | | | | | |
| Batch 1 | 50 | 13.2 | 660 | 35.8 | 0.0069 | 4.554 | 164.5 | 4.6 |
| Batch 2 | 50 | 18.4 | 920 | 28.3 | 0.012 | 11.04 | 67.94 | 2.4 |
| 3. Acetone Precipitation | | | | | | | | |
| Batch 1 | 20 | 12.3 | 246 | 13.3 | 0.052 | 12.792 | 462.1 | 34.7 |
| Batch 2 | 20 | 15.0 | 300 | 9.23 | 0.090 | 27.00 | 166.2 | 18 |

*One unit of enzyme activity was here defined as that amount of enzyme that catalyzes the conversion of one μmole of bilirubin per minute at pH 7.45 ± 0.05 and 22°–25° C. Specific activity (S.A.) is then the activity unit divided by mg of protein used per assay.

**For all activity assays, a 2mg/dl bilirubin solution was used. The control omitted the substrate but otherwise had the same composition as the test cuvette. The molar absorptivity at 440 nm of bilirubin was assumed to be about $55 \times 10^3$. This was used in calculating the activity units.

Part C—Bilirubin Specificity

1. The procedure of Example 2, Part B, was repeated except that the enzyme preparation was prepared according to the procedure described in Part A of this Example. Again, no changes in the spectra of hemoglobin and biliverdin were detected, verifying that the enzyme preparation obtained by the method of the present invention is specific for bilirubin.

2. A second method was also used in this Part to determine enzyme specificity. The reaction mixtures were prepared as described above, but the reactions were evaluated fluorometrically by exciting the mixtures at 450 nm and monitoring emission at 525 nm in a Turner Model 420 spectrofluorometer (G. K. Turner Associates, Palo Alto, California). Individual aqueous reaction mixtures of bilirubin, hemoglobin, biliverdin, or enzyme preparation alone had minimal background fluorescence at this wavelength, but the bilirubin-enzyme mixture showed increases in fluorescence intensity that paralleled increases in time or bilirubin concentration levels (0.1-4 mg/dl, tested range). No such fluorescence changes were visible with hemoglobin or biliverdin when the enzyme was present for as long as ½ hour.

Part D—Effect of Enzyme Concentration

Varying levels of the enzyme preparation extracted as described in Part A of this Example were added to solutions containing 2 mg/dl of freshly prepared bilirubin in 0.05 M sodium phosphate buffer, pH 7.4±0.05 at 22°–25° C. and an assay was conducted as described in Procedure 2. Plotting of the data in Table V below shows a nearly linear relationship between the initial velocity, $V_i$, ($\Delta A_{440\ nm}/min$) and the amount of enzyme protein used per assay.

Table V

| Enzyme Preparation (μg. protein) | Initial Velocity, $V_i$, ($\Delta A_{440nm}/min$) |
|---|---|
| 80 | 0.12 |
| 160 | 0.23 |
| 240 | 0.32 |
| 400 | 0.46 |
| 720 | 0.67 |

Part E—Effect of Bilirubin Concentration

Test conditions were the same as in Part D of this Example, except that 10 μl samples (about 0.6 mg protein) of the enzyme preparation were added to varying amounts of bilirubin solution (0-5 mg/dl) in each sample. Due to the high absorbance of bilirubin solutions, kinetics at concentrations above 3 mg/dl were not obtainable. The data thus obtained illustrated a highly linear relationship between the initial velocity of bilirubin degradation by the enzyme preparation and the bilirubin concentration. Based on a Lineweaver-Burk linear transformation of the available data (see Lineweaver and Burk, supra), the apparent extrapolated $K_m$ of the enzyme was $15.4 \times 10^{-4}$ M, whereas a nonlinear transform (which appeared to better fit the actual data points) gave an apparent $K_m$ of $4 \times 10^{-5}$ M, corresponding to 24 mg/dl bilirubin.

Part F—One-Minute Assay for Bilirubin by Enzyme

Ten microliter samples (about 0.8 mg) of the enzyme preparation obtained as in Part A were added last to assay reaction mixtures containing from 0-5 mg/dl bilirubin buffered with 0.05 M sodium phosphate at pH 7.45±0.05. The final volume of each assay reaction mixture was 1.01 ml. The actual absorbance of bilirubin measured after 1 minute at 440 nm in the absence of and in the presence of enzyme preparation is shown in Columns 2 and 3, respectively, of Table VI. The difference between Columns 2 and 3 of Table VI illustrates a clear-cut decrease in absorbance ($A_{440}$ nm) after one-minute action by the enzyme at every level of substrate tested. In each of the assays of this part, the decrease in absorbance ($\Delta A_{440\ nm}$) was also monitored after 1 minute incubation at pH 7.4 at 22° C. against a reference cuvette of identical enzyme preparation composition, except that bilirubin was omitted.

Table VI

| 1 (mg/dl bilirubin) | 2 (Absolute absorbance at 440nm after 1 minute in the absence of enzyme preparation) | 3 (Absolute absorbance at 440nm after 1 minute in the presence of the enzyme preparation) |
|---|---|---|
| 0 | 0 | 0 |
| 0.5 | 0.40 | 0.25 |
| 1.0 | 0.65 | 0.40 |
| 2.0 | 1.35 | 0.72 |
| 3.0 | 1.92 | 1.03 |
| 5.0 | 2.85 | 1.55 |

Part G—Assay Coupling Hydrogen Peroxide-Generating, Bilirubin-Specific Enzyme to Hydrogen Peroxide Detection Composition Varying concentrations of bilirubin (0–5 mg/dl) were added to a series of assay reaction mixtures containing: 50 μl of a 1% fresh solution of o-phenylene-diamine in 0.05 M sodium phosphate, pH 7.45±0.05, 10 μl of peroxidase solution prepared by Procedure 1 of this Example, and an amount of enzyme preparation obtained as in Part A of this Example and containing about 0.78 mg of protein. (A control reaction mixture contained everything except the enyzme preparation.) Each assay reaction mixture was incubated at 25° C. for 2–3 minutes and the reaction was followed photometrically by measuring the increase in absorbance of the oxidized o-phenylene-diamine dye at 550 nm. Table VII depicts the strikingly linear relationship between the initial velocity, $V_i$($\Delta A_{440\ nm}/min$) and bilirubin concentrations, i.e., $V_i$ increases with increasing bilirubin levels. These results indicated hydrogen peroxide was formed during the fungal enzyme reaction in quantities that correlated with the concentration of bilirubin.

Table VII

| Bilirubin concentration | $V_i$ ($\Delta A_{440nm}/min$) |
|---|---|
| 0.0 | 0 |
| 0.5 | 0.07 |
| 1.0 | 0.13 |
| 2.0 | 0.28 |
| 3.0 | 0.35 |
| 5.0 | 0.52 |

The invention has been described in detail with particular reference to certain preferred embodiments thereof, but it will be understood that variations and modifications can be effected within the spirit and scope of the invention.

I claim:

1. A bilirubin-specific enzyme preparation comprising a fungal enzyme which, in the presence of a bilirubin-containing aqueous liquid having a pH of about 7.4 and a temperature of about 37° C., degrades at least about 0.02 micromoles of bilirubin per minute per milligram of protein.

2. A bilirubin-specific enzyme preparation as described in claim 1 which, in the presence of a bilirubin-containing aqueous liquid maintained at a pH of about 7.4 and a temperature of 37° C., yields a detectable reaction product that exhibits an absorption peak at about 510 nm and that, upon excitation with 450 nm radiation, exhibits fluorescence emission at about 525 nm.

3. A bilirubin-specific enzyme preparation as described in claim 1 derived from mushroom.

4. A bilirubin-specific enzyme preparation comprising a fungal enzyme which, in the presence of a bilirubin-containing aqueous liquid having a pH of about 7.4 and a temperature of about 37° C., degrades at least about 0.02 micromoles of bilirubin per minute per milligram of protein and generates hydrogen peroxide.

5. A bilirubin-specific enzyme preparation as described in claim 4 which, in the presence of a bilirubin-containing aqueous liquid maintained at a pH of about 7.4 and a temperature of 37° C., yields a detectable reaction product that exhibits an absorption peak at about 510 nm and that, upon excitation with 450 nm radiation, exhibits fluorescence emission at about 525 nm.

6. A bilirubin-specific enzyme preparation as described in claim 4 derived from mushroom.

7. An assay composition for the determination of bilirubin in an aqueous liquid, said composition comprising a hydrogen-peroxide detection composition and a bilirubin-specific enzyme preparation comprising a mushroom enzyme which, in the presence of a bilirubin-containing aqueous liquid having a pH of about 7.4 and a temperature of about 37° C., degrades at least about 0.02 micromoles of bilirubin per minute per milligram of protein and generates hydrogen peroxide.

8. An assay composition as described in claim 7 wherein said assay composition contains a buffer.

9. An assay composition as described in claim 7 wherein said hydrogen peroxide detection composition comprises a material having peroxidative activity and a chromogenic indicator.

10. An assay composition as described in claim 7 wherein said hydrogen peroxide detection composition comprises peroxidase and a chromogenic indicator.

11. A dry test element for the assay of an aqueous liquid, said element having a reagent zone containing an assay composition for bilirubin, said assay composition for bilirubin comprising a mushroom enzyme preparation which, in the presence of a bilirubin-containing aqueous liquid having a pH of about 7.4 and a temperature of about 37° C., degrades at least about 0.02 micromoles of bilirubin per minute per milligram of protein.

12. A method for the determination of bilirubin in an aqueous liquid sample comprising
(a) contacting said liquid sample with a bilirubin-specific enzyme preparation to interact bilirubin with said enzyme preparation and produce a detectable change, said enzyme preparation containing a mushroom enzyme which, in the presence of a bilirubin-containing aqueous liquid having a pH of about 7.4 and a temperature of about 37° C., degrades at least about 0.02 micromoles of bilirubin per minute per milligram of protein; and
(b) detecting said change.

13. A method for the determination of bilirubin in an aqueous liquid sample comprising
(a) contacting said liquid sample with an assay composition containing a hydrogen-peroxide detection composition and a bilirubin-specific enzyme preparation to interact bilirubin with said enzyme preparation and produce a detectable change, said enzyme preparation containing a mushroom enzyme which, in the presence of a bilirubin-containing aqueous liquid having a pH of about 7.4 and a temperature of about 37° C., degrades at least about 0.02 micromoles of bilirubin per minute per milligram of protein and generates hydrogen peroxide; and
(b) detecting said change.

14. The method as described in claim 13 wherein said contacting step is carried out at a pH within the range of from about 7.3 to about 8.0 and a temperature of from about 20° to 50° C.

15. An assay method for the determination of an analyte other than bilirubin in an aqueous liquid sample containing bilirubin, bilirubin being an interferent for said assay method, said method comprising
(a) treating said samples with an interactive composition for said analyte to produce a detectable change,
(b) prior to or during step (a), contacting said sample with a bilirubin-specific enzyme preparation containing a mushroom enzyme which, in the presence of a bilirubin-containing aqueous liquid having a pH of about 7.4 and a temperature of about 37° C., degrades at least about 0.02 micromoles of bilirubin per minute per milligram of protein, thereby degrading bilirubin and reducing its potential for interference with the detectable change produced in step (a), and
(c) detecting said change produced in step (a).

16. A method for the extraction of a bilirubin-specific, fungal enzyme preparation comprising
(a) blending mushroom with an aqueous buffer solution having a pH of about 6.8 to 7.8 to form a homogeneous aqueous mixture,
(b) separating insoluble solids from said aqueous mixture to obtain an aqueous liquid supernatant,
(c) treating said supernatant with a water-soluble salt to produce a precipitate,
(d) suspending said precipitate in an aqueous buffer solution having a pH of about 6.8 to 7.8 to form a suspension,
(e) heating said suspension above about 22° C. but below the boiling point thereof,
(f) cooling said suspension and separating solids from said suspension to recover an aqueous liquid supernatant representing a bilirubin-specific fungal enzyme preparation, each of said steps a, b, c, d, and f carried out at a temperature of from about 0° to 4° C.

17. A method for the extraction of a bilirubin-specific, fungal enzyme preparation comprising the following steps carried out at a temperature of from about 0° to 4° C.:
(a) blending mushroom with an aqueous buffer solution having a pH of about 6.8 to 7.8 to form a homogeneous aqueous mixture,
(b) separating insoluble solids from said aqueous mixture to obtain an aqueous liquid supernatant,
(c) treating said supernatant with a water-soluble salt to produce a precipitate, (d) suspending said precipitate in an aqueous buffer solution having a pH of about 6.8 to 7.8 to form a suspension, (e) treating said suspension with a water-miscible organic liquid chilled to a temperature effective to produce a precipitate from said resulting aqueous-organic liquid mixture, (f) repeating step (d) and (e) at least one time using as said precipitate in said repeat of step (d) the precipitate produced in step (e), and (g) recovering the precipitate remaining following the last repeat of step (e) to obtain a bilirubin-specific, hydrogen peroxide-generating fungal enzyme preparation.

18. An assay composition for the determination of bilirubin in an aqueous liquid, said composition comprising a hydrogen-peroxide detection composition and a bilirubin-specific enzyme preparation comprising a fungal enzyme which, in the presence of a bilirubin-containing aqueous liquid having a pH of about 7.4 and a temperature of about 37° C., degrades at least about 0.02 micromoles of bilirubin per minute per milligram of protein and generates hydrogen peroxide.

19. A dry test element for the assay of an aqueous liquid, said element having a reagent zone containing an assay composition for bilirubin, said assay composition for bilirubin comprising a fungal enzyme preparation which, in the presence of a bilirubin-containing aqueous liquid having a pH of about 7.4 and a temperature of about 37° C., degrades at least about 0.02 micromoles of bilirubin per minute per milligram of protein.

20. A method for the determination of bilirubin in an aqueous liquid sample comprising (a) contacting said liquid sample with a bilirubin-specific enzyme preparation to interact bilirubin with said enzyme preparation and produce a detectable change, said enzyme preparation containing a fungal enzyme which, in the presence of a bilirubin-containing aqueous liquid having a pH of about 7.4 and a temperature of about 37° C., degrades at least about 0.02 micromoles of bilirubin per minute per milligram of protein; and (b) detecting said change.

* * * * *